(12) United States Patent
Ragauskas et al.

(10) Patent No.: US 9,168,023 B2
(45) Date of Patent: Oct. 27, 2015

(54) METHOD AND APPARATUS FOR CONTINUOUSLY MONITORING INTRACRANIAL PRESSURE

(75) Inventors: Arminas Ragauskas, Kaunas (LT); Gediminas Daubaris, Kaunas (LT); Vytautas Petkus, Kaunas (LT); Renaldas Raisutis, Kaunas (LT)

(73) Assignee: UAB Vittamed (LT)

( * ) Notice: Subject to any disclaimer, the term of this patent is extended or adjusted under 35 U.S.C. 154(b) by 786 days.

(21) Appl. No.: 13/487,619

(22) Filed: Jun. 4, 2012

(65) Prior Publication Data
US 2012/0238885 A1 Sep. 20, 2012

Related U.S. Application Data

(62) Division of application No. 12/121,161, filed on May 15, 2008, now Pat. No. 8,926,515.

(51) Int. Cl.
*A61B 8/00* (2006.01)
*A61B 8/10* (2006.01)
*A61B 5/03* (2006.01)
*A61B 5/00* (2006.01)
*A61B 8/06* (2006.01)

(52) U.S. Cl.
CPC . *A61B 8/10* (2013.01); *A61B 5/031* (2013.01); *A61B 5/6843* (2013.01); *A61B 8/06* (2013.01); *A61B 8/4209* (2013.01); *A61B 8/4227* (2013.01)

(58) Field of Classification Search
None
See application file for complete search history.

(56) References Cited

U.S. PATENT DOCUMENTS

| | | | | | |
|---|---|---|---|---|---|
| 4,204,547 | A | * | 5/1980 | Allocca | 600/561 |
| 4,907,595 | A | * | 3/1990 | Strauss | 600/452 |
| 4,930,513 | A | * | 6/1990 | Mayo et al. | 600/455 |
| 4,984,567 | A | * | 1/1991 | Kageyama et al. | 600/438 |
| 5,016,641 | A | | 5/1991 | Schwartz | |
| 5,040,540 | A | | 8/1991 | Sackner | |
| 5,117,835 | A | * | 6/1992 | Mick | 600/561 |
| 5,388,583 | A | * | 2/1995 | Ragauskas et al. | 600/451 |
| 5,951,477 | A | * | 9/1999 | Ragauskas et al. | 600/438 |
| 6,086,533 | A | * | 7/2000 | Madsen et al. | 600/438 |
| 6,309,354 | B1 | * | 10/2001 | Madsen et al. | 600/438 |
| 6,547,734 | B2 | * | 4/2003 | Madsen et al. | 600/438 |
| 6,875,176 | B2 | * | 4/2005 | Mourad et al. | 600/442 |

(Continued)

OTHER PUBLICATIONS

Bor-Sen-Shu, et al.; "Cerebral Hemodynamic Changes Gauged by Transcranial Doppler Ultrasonography in Patients with Post-traumatic Brain Swelling Treated by Surgical Decompression"; J Neurosurg 104:93-100; 2006.

(Continued)

*Primary Examiner* — Nicholas Evoy
(74) *Attorney, Agent, or Firm* — St. Onge Steward Johnston & Reens LLC

(57) ABSTRACT

A method and apparatus for continuously measuring the absolute intracranial pressure in a non-invasive manner is described by using an ultrasonic Doppler device which detects the pulsatility indexes of the blood flow inside the eye artery for both intracranial and extracranial eye artery portions. The eye in which the blood flow is monitored is subjected to a small pressure, sufficient to equalize the pulsatility index measurements of the internal and external portions of the eye artery. The pressure at which such equalization occurs is used as a reference for autocalibration of the apparatus so that continuous absolute intracranial pressure measurements may be taken over a particular sampling period.

8 Claims, 3 Drawing Sheets

(56) References Cited

U.S. PATENT DOCUMENTS

| | | | |
|---|---|---|---|
| 7,122,007 B2* | 10/2006 | Querfurth | 600/485 |
| 7,403,805 B2* | 7/2008 | Abreu | 600/318 |
| 7,547,283 B2* | 6/2009 | Mourad et al. | 600/459 |
| 7,559,898 B2* | 7/2009 | Eide | 600/485 |
| 7,654,957 B2* | 2/2010 | Abreu | 600/399 |
| 8,398,564 B2* | 3/2013 | Eide | 600/561 |
| 8,647,278 B2* | 2/2014 | Ji et al. | 600/454 |
| 8,926,515 B2* | 1/2015 | Ragauskas et al. | 600/454 |
| 2002/0052550 A1* | 5/2002 | Madsen et al. | 600/438 |
| 2004/0059220 A1* | 3/2004 | Mourad et al. | 600/442 |
| 2004/0230124 A1* | 11/2004 | Querfurth | 600/485 |
| 2005/0015009 A1* | 1/2005 | Mourad et al. | 600/438 |
| 2006/0241459 A1* | 10/2006 | Tai | 600/454 |
| 2007/0016031 A1* | 1/2007 | Mourad et al. | 600/437 |
| 2009/0287084 A1* | 11/2009 | Ragauskas et al. | 600/454 |
| 2010/0010322 A1* | 1/2010 | Brady | 600/301 |

OTHER PUBLICATIONS

Schmidt, et al.; "Clinical Applications of a Non-Invasive ICP Monitoring Method"; European Journal of Ultrasound 16 (2002) 37-45.

Bellner, et al.; "Transcranial Doppler Sonography Pulsatility Index (PI) Reflects Intracranial Pressure (ICP)"; Surg. Neurol 2004; 62:45-51.

* cited by examiner

METHOD AND APPARATUS FOR CONTINUOUSLY MONITORING INTRACRANIAL PRESSURE

CROSS-REFERENCE TO RELATED APPLICATIONS

This patent application is a divisional of currently pending U.S. patent application Ser. No. 12/121,161, filed May 15, 2008 now U.S. Pat. No. 8,926,515, the content of which is incorporated herein by reference.

FIELD OF THE INVENTION

The present invention generally relates to a method and apparatus for continuously and non-invasively monitoring intracranial pressure, and more specifically relates to an improved method and apparatus for continuously determining intracranial pressure using ultrasonic measurements of the velocity of blood flow through an eye artery.

BACKGROUND OF THE INVENTION

This invention is an extension and improvement of our previously invented method and apparatus U.S. Pat. No. 5,951,477 (the '477 patent) for single or single repeatable absolute intracranial pressure (ICP) value measurement and diagnosing of brain pathologies based on such measurements. This document is incorporated by reference in the present application.

The '477 patent teaches an apparatus and method for deriving an indication of intracranial pressure in a non-invasive manner using an ultrasonic Doppler measuring technique that is applied to the eye artery. In one aspect, this is achieved by a chamber which can apply a slight pressure to the eye and an ultrasonic apparatus which can simultaneously measure the internal and external blood flows in the eye artery. Signals representative of these velocity measurements, $V_I$ and $V_E$ are then compared and their difference, $\Delta V$, is used to control the pressure in the chamber. When the pressure in the chamber causes $\Delta V$ to approach a desired minimum value, that pressure becomes an indication of the intracranial pressure.

One disadvantage of the method and apparatus taught in the 477' patent is that it is impossible to continuously and non-invasively monitor the absolute ICP value. Continuous monitoring of absolute ICP value is one of the aims of the US and EU traumatic brain injury management guidelines.

Therefore, one objective of the present invention is the continuous non-invasive monitoring of absolute ICP value. To achieve this objective, we non-invasively determine an absolute intracranial pressure value $Po_i$ in i-th measurement cycle using the method and apparatus taught in the '477 patent. This non-invasive measurement of $Po_i$ is then used as a single autocalibration procedure for the non-invasive ICP monitor during i-th time interval of ICP monitoring, and becomes the initial value of the absolute ICP scale for the next continuous absolute ICP monitoring cycle, $Po_{(i+1)}$. After the time of continuous ICP monitoring during (i+1)-th time interval, the next single autocalibration procedure is performed and new value $Po_{(i+2)}$ is identified. That value is used as the initial value of the absolute ICP scale for the next continuous absolute ICP monitoring cycle. This process is repeated for the desired number of monitoring cycles.

When several $Po_i$ data points are collected, a conversion factor $\Omega$ can be determined as a function of pulsatility indexes for a wider interval of absolute ICP values. Stability of the conversion factor dictates whether the time interval of continuous ICP monitoring should be decreased, or increased. If the conversion factor $\Omega$ is stable, the continuous absolute ICP monitoring time interval can be increased. If the conversion factor and the pathophysiological conditions of the patient are changing, the continuous absolute ICP monitoring time interval must be decreased.

Advantages of the present invention are that the absolute ICP monitoring is continuous and the external pressure Pe is used only for autocalibration of the system "individual patient—non-invasive ICP meter". In the '477 patent, it was necessary to apply external pressure Pe to the eye for the entire sampling period of discrete absolute ICP monitoring. Thus, the added value of the invention is the possibility to obtain important information about absolute ICP value non-invasively and continuously between two single absolute ICP measurements which are used for the system's autocalibration.

SUMMARY OF THE INVENTION

Accordingly, it is an object of the present invention to provide a non-invasive method and apparatus for continuous absolute ICP monitoring.

In order to overcome the deficiencies of the prior art and to achieve at least some of the objects and advantages listed, an embodiment of the apparatus for continuously obtaining an indication of intracranial pressure comprises a device for measuring the pulsatility index of blood flow in the intracranial portion of an eye artery (P.I.(int)) and generating an internal pulsatility index signal representative thereof, and measuring the pulsatility index of blood flow in the extracranial portion of an eye artery (P.I.(ext)) and generating an external pulsatility index signal representative thereof; a device for applying an external pressure against an eye, measuring the external pressure applied against the eye, and generating an external pressure signal representative of the measured external pressure; and a processor for receiving the external pressure signal, the internal pulsatility index signal, and the external pulsatility index signal and calculating a conversion factor ($\Omega$) therefrom for converting said internal pulsatility index signal and said external pulsatility index signal into an indication of continuous absolute intracranial pressure.

The device for continuously measuring the pulsatility index of blood flow in the intracranial portion of an eye artery and measuring the pulsatility index of blood flow in the extracranial portion of an eye artery may be provided as an ultrasonic Doppler device.

Conversion factor ($\Omega$) may be calculated as the value of the measured external pressure which causes the ratio of the external pulsatility index (P.I.(ext)) to the internal pulsatility index (P.I.(int)) to become equal to one (1). Additionally, the indication of continuous absolute intracranial pressure (ICP) may be calculated from the formula ICP=$\Omega$ (P.I.(ext)/P.I.(int)) and it may be calculated for at least on sampling period. The processor may also calculate a value of said conversion factor ($\Omega$) for each of the at least one sampling periods.

The processor provided in one embodiment may also determine whether the conversion factor is stable by comparing the value of the conversion factor for each of the at least one sampling periods. The conversion factor is stable if there is an insubstantial change in the value of the conversion factor for each of the at least one sampling periods. If the conversion factor is stable, the length of each of the at least one sampling periods may be increased. If the conversion factor is not stable, the length of each of the at least one sampling periods may be decreased.

An embodiment of a method for continuously obtaining an indication of absolute intracranial pressure is also provided. The method may comprise the steps of: A) measure the pulsatility index of blood flow in the intracranial portion of an eye artery (P.I.(int)); B) measure the pulsatility index of blood flow in the extracranial portion of an eye artery (P.I.(ext)); C) apply an external pressure against an eye and measure said external pressure applied against the eye; D) calculate a ratio of P.I.(ext) to P.I.(int); E) calculate a conversion factor to convert the ratio of P.I.(ext) to P.I.(int) into intracranial pressure, wherein said conversion factor is equal to the external pressure measured which causes said ratio of P.I.(ext) to P.I.(int) to become equal one (1); and F) repeat steps A, B, and D and determine intracranial pressure (ICP) by applying said conversion factor to the calculated ratio of P.I.(ext) to P.I.(int).

The method may also comprise the steps of: G) periodically repeat steps A-E; and I) repeat step F. In another embodiment, the method of claim further comprises the step of: J) determine whether the conversion factor is stable by comparing the value of the conversion factor calculated in steps E and G. In yet another embodiment, the method further comprises the step of: K) determine that the conversion factor is stable if there is an insubstantial change in the value of the conversion factor calculated in steps E and G.

DETAILED DESCRIPTION OF THE INVENTION

We have found that with the apparatus in accordance with the present invention, the absolute value of intracranial pressure can be monitored continuously and non-invasively.

Figure 1:
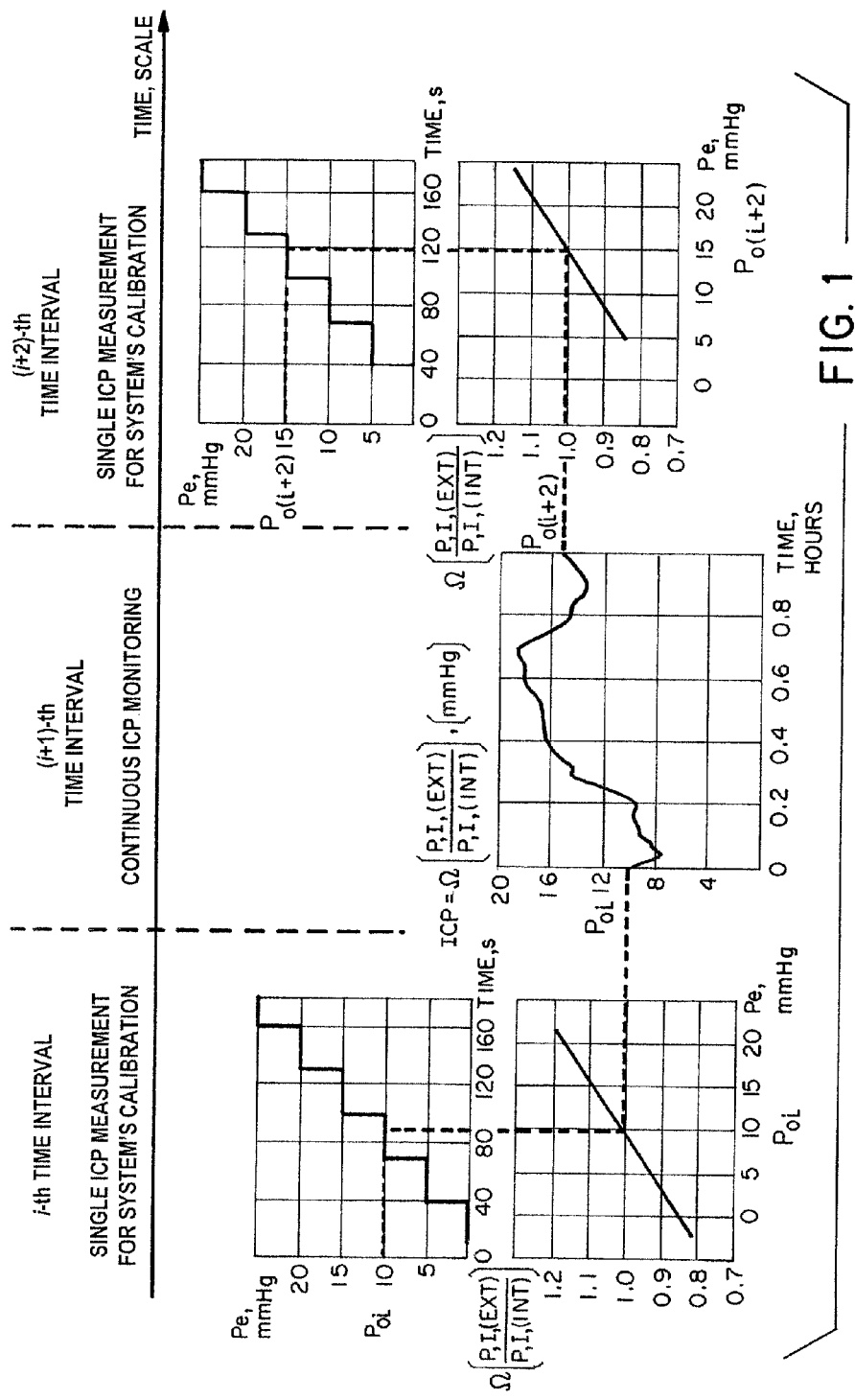
FIG. 1 is a time chart of non-invasive absolute ICP continuous monitoring device.

As shown in FIG. 1, the present invention involves an apparatus for non-invasively determining an absolute intracranial pressure value $Po_i$ in i-th measurement cycle. Using the method and apparatus taught in the '477 patent, the intracranial pressure value $Po_i$ is determined by applying an extracranial pressure $P_e$ to the eye over some time interval, for example 200 seconds. During that interval, $P_e$ is increased step-by-step from 0 mmHg to 25.0 mmHg, at 5.0 mmHg increments, until the ratio of extracranial to intracranial pulsatility indexes P.I.(ext)/P.I.(int) of blood flow in the intracranial and extracranial segments of the eye artery (ophthalmic artery) becomes equal to 1.0.

Pulsatility index PI is defined by the ratio (Vsyst−Vdiast)/Vmean, where Vsyst the systolic blood flow velocity value, Vdiast is the diastolic blood flow velocity value, and Vmean is the mean value of blood flow. Blood flow velocities are measured by a two-depth transcranial Doppler (TCD) device in both the intracranial and extracranial segment of the eye artery. Thus, both pulsatility indexes P.I.(int) in the intracranial segment and P.I.(ext) in the extracranial segment of eye artery are defined using results of Vsyst, Vdiast and Vmean measurement.

The non-invasive measurement of $Po_i$ is used as a single autocalibration procedure for the non-invasive ICP monitor during i-th time interval of ICP monitoring. The value of $Po_i$ also becomes the initial value of the absolute ICP scale for the first continuous absolute ICP monitoring cycle, $Po_{(i+1)}$.

Continuous monitoring of absolute ICP data begins from $Po_{(i+1)}$ (e.g., $Po_i=10$ mmHg in FIG. 1). ICP is continuously and non-invasively monitored using the ratio of the pulsatility indexes, i.e., P.I.(ext)/P.I.(int). Once the ratio is known, we can calculate ICP=Ω(P.I.(ext)/P.I.(int)), where Ω is a conversion factor for converting pulsatility indexes into absolute non-invasive ICP values. Conversion factor Ω is individual to each patient and depends on the physiological state of the patient, i.e., arterial blood pressure, cerebrospinal compliance, etc.

After the time of continuous ICP monitoring during (i+1)-th measurement cycle (e.g., 1 hour in FIG. 1), the next single autocalibration procedure—non-invasive measurement of absolute ICP $Po_{(i+2)}$—is performed and new value $Po_{(i+2)}$ is identified. That value is used as the initial value of the absolute ICP scale for the next continuous absolute ICP monitoring cycle. This process is repeated for the desired number of monitoring cycles.

When several $Po_i$ data points are collected, values of conversion factor Ω can be determined as a function of ICP for a wider interval of absolute ICP values. Stability of the conversion factor as a function of time can also be checked. The conversion factor is stable if there is in an insubstantial change in its value over time. If the conversion factor Ω is stable, the continuous absolute ICP monitoring time interval can be increased. If the conversion factor and the pathophysiological conditions of the patient are changing, the continuous absolute ICP monitoring time interval must be decreased. In practice, a single absolute ICP non-invasive measurement time for the system's calibration is much shorter than the fifteen (15) minute continuous non-invasive absolute ICP monitoring time.

Figure 2:
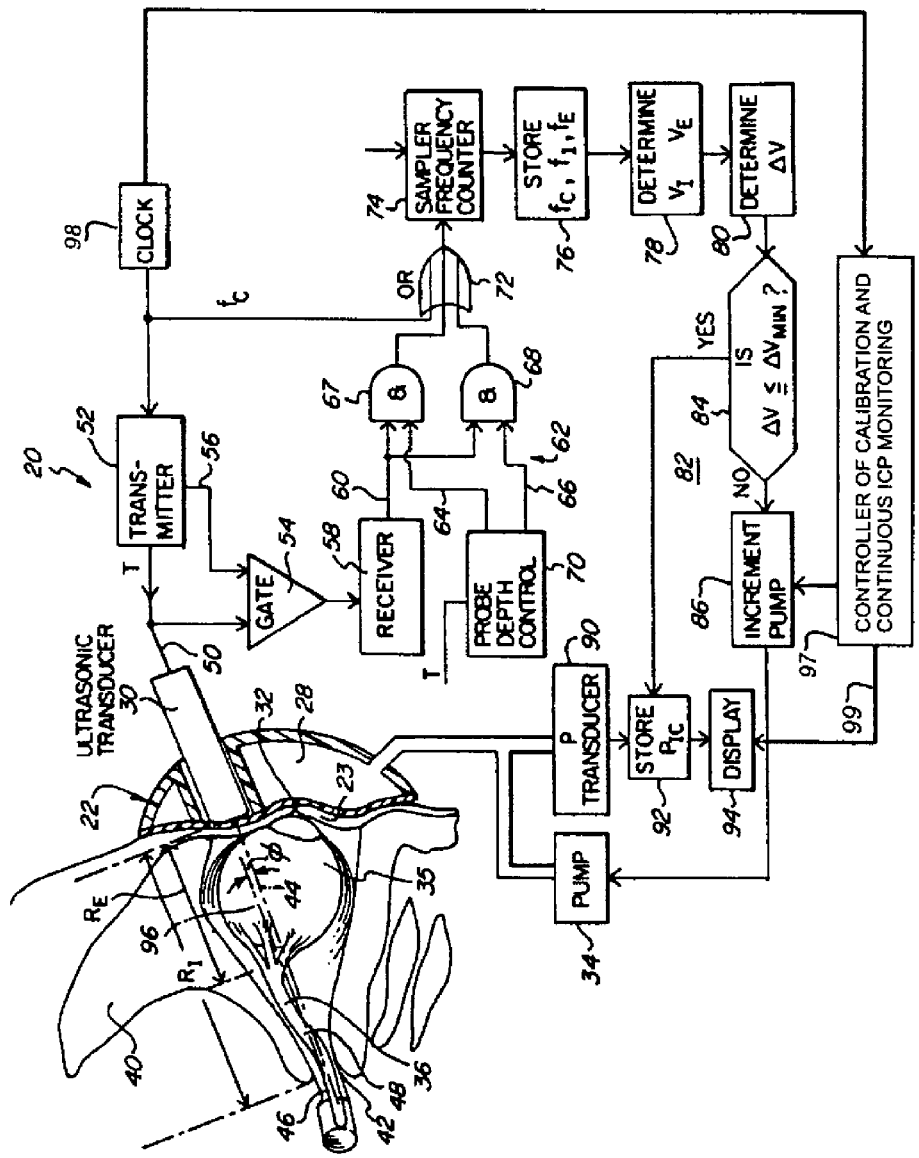
FIG. 2 is a structural diagram of the apparatus for non-invasive absolute ICP continuous monitoring.

With reference to FIG. 2, an apparatus 20 is shown to practice the continuous measurement of the intracranial pressure as described above. The apparatus is mountable to the head of a person so that an eye engaging inflatable device 22 can apply a slight pressure against the eye lid 23. Suitable braces and positioning bands 24, 26 are used to hold the device 22 in place. The device 22 is formed of a suitable soft material such as rubber or other polymer film to form an inflatable chamber 28. Chamber 28 is approximately annular in shape so as to enable an ultrasonic transducer 30 to be mounted against an inner flexible membrane 32 and enable a pressurization of the chamber by a pump 34.

The inner membrane conforms to the shape of the eye 35 as illustrated and in such manner enables the pressure from the inflation of chamber 28 to provide a slight pressurization of the tissues surrounding the eye and thus the eye socket. This results in a pressurization of the eye artery 36, which originates from inside the cranium 40 and passes through the optic nerve canal 42 to the eye 35.

The ultrasonic transducer 30 has a central axis 44, which can be aligned by adjusting the position of the transducer inside its mounting to device 22. This alignment allows one to adjust the angle of axis 44 so as to direct its ultrasonic acoustic pulses at both interior and exterior portions 46, 48 of the eye artery 36 at the same angle. With such alignment, Doppler measurements of the blood flow velocities in these different portions 46, 48 can be made without the introduction of errors from the use of different angles of axis 44 with respect to portions 46 and 48. Hence, a reliable measurement of the intracranial and extracranial pulsatility indexes, P.I.(int) and P.I.(ext) respectively, can be determined.

The ultrasonic transducer 30 has its input line 50 coupled to an acoustic pulse transmitter 52. The transducer 30 also acts as a sonic receiver so that its input line 50 is connected to a gate 54. A gate input 56 is connected to the transmitter 52 to protect a receiver 58 from the high transmitter output pulses during pulsing of the transducer 30. The receiver 58 produces an output signal on line 60 representative of the acoustic echoes from the blood flow in the eye artery OA and caused by the ultrasonic pulses from the transmitter 52.

A depth control network 62 is provided to enable the apparatus 20 to select that portion of received echoes representative of either the internal or external, cranium, eye artery, blood velocities. The network 62 produces an internal selection signal on line 64 and an external selection signal on line 66. The internal selection signal is applied to an AND gate 67 to enable the echoes related to the blood flow inside the cranium to be selected for further processing. Similarly, the external signal is applied to an AND gate 68 to select the echoes related to the blood flow in the eye artery external of the cranium. The network 62 operates as a range gating system with which acoustic returns of different depths can be selected and analyzed for their Doppler frequency shift relative to the transmitter frequency $f_c$.

The internal and external selection signals are generated in sequence in a manner as is well known by a control 70 activated after each transmitter pulse by the signal on line 56. The outputs from AND gates 67, 68 are coupled through an OR gate 72 to a sampler frequency counter 74. This samples the received echo signals and produces sample signals, such as the signal frequency, $f_I$, in the pulse representative of blood velocity inside the cranium, the signal frequency, $f_E$, inside the echo pulse from the eye artery external of the cranium, and the frequency, $f_C$, in the transmitted pulse. The sampled frequency signals are stored at 76 in a suitable memory and at 78 the shifts in the frequencies from the frequency of the transmitted pulse, such as $f_C-f_I$ and $f_C-f_E$, are determined. A suitable microprocessor can be used to implement these functions.

The frequency shifts can be determined for each transmitter pulse and resulting echo. Each frequency shift is representative of the blood velocity in the eye artery and the values can be so stored to provide an indication of the internal blood velocity, $V_I$, and external blood velocity, $V_E$, at 78. The velocity difference value $\Delta V$ at 80 can then be displayed and the display is used to determine the intracranial pressure.

The difference values $\Delta V$ are used to determine the intracranial pressure $Po_i$. This is done by increasing the pressure inside the inflatable device 22 to a level where ratio of the intracranial and extracranial pulsatility indexes (which depend on the value of $\Delta V$) becomes equal to one. The $Po_i$ measurement can be made by manually increasing the pressure inside the device 22 until the visual indications of the measured pulsatility indexes P.I.(int) and P.I.(ext), or the frequency shifts, appear the same or with an automatic control such as 82.

Alternatively an automatic control 82 can be implemented, for example, by first testing at 84 whether the value of $\Delta V$ is below a minimum value such as $\Delta V_{min}$. If not, then at 86 a value for the pump pressure is incremented and its value applied to pump 34 to cause it to increase the pressure $P_e$ inside the inflatable device 22. A pressure transducer 90 senses the pressure inside the chamber 28.

When the test at 84 shows positive, the value $P_e$ is stored at 92 as an indication of the intracranial pressure, $Po_i$. This can be displayed at 94 and suitably recorded.

In the operation of apparatus 20, it desirable that an initial alignment mode be undertaken to assure that the transmitter pulses from the transducer 30 are properly directed at both the internal and external portions 46 and 48 of the eye artery 36. This involves adjustments in the angle $\phi$ between the axis 44 of the ultrasonic transducer 30 and the alignment axis 96 of the eye artery passage 42.

A controller 97 of continuous ICP monitoring is added to the structural diagram of previously invented method and apparatus of the '477 patent. The additional controller 97 is connected with clock 98 and increment pump 86. The controller 97 manages i-th measurement cycles, performs pressure $P_e$ increments of the pump 34, calculates the ratio of pulsatility indexes P.I.(ext)/P.I. (int), compares it with the predetermined 1.0 value, and calibrates the non-invasive ICP monitoring display 94 by the output signal 99.

Figure 3:
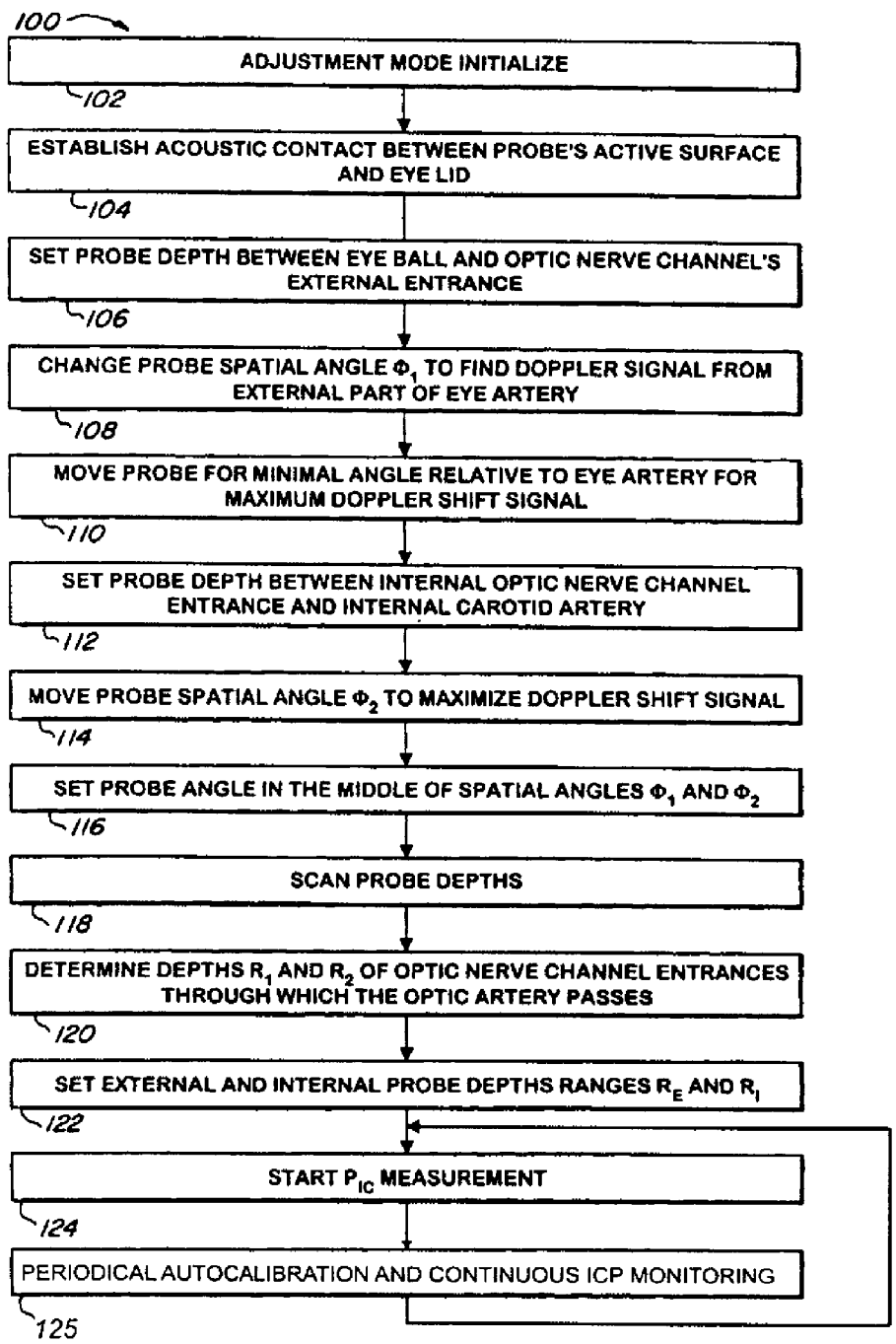
FIG. 3 is an algorithm of the apparatus for non-invasive absolute ICP continuous monitoring.

With reference to FIG. 3, a routine 100 for making such alignment is illustrated. Thus at 102 the apparatus 20 is initialized and at 104 operative contact between the acoustic transmitter 30 and the eye cavity is established by observing return echoes on a display. At 106 the depth of the operative probe depth $R_E$, see FIG. 1, is entered by the probe depth control block 70 (See FIG. 1). Typical initial values of $R_E$ are approximately between 40 mm and 50 mm.

At 108 the spatial angle $\phi$ of the transducer axis 44 is changed to find the velocity signal associated with the extracranial eye artery portion 48. This is found by observing the shape of the blood velocity pulsation curve of the extracranial part 48 of the eye artery 44, (see FIG. 5). The spatial angle, $\phi_1$, which yields the maximum Doppler signal level, is selected at 110 and noted.

At 112, the initial value of the internal probe depth $R_I$ is entered by the control block 70. The typical values of $R_I$ are approximately between 52 mm and 65 mm.

At 114 the spatial angle $\phi_2$ is determined for the alignment of the transducer 30 yielding the maximum Doppler signal pulsation from the internal portion 46 of the eye artery 36. The operating orientation of the transducer 30 is the selected at 116 by aligning the axis 44 of the transducer 30 along the middle between the angles $\phi_1$ and $\phi_2$.

Then at 118 the probe depth control 70 is actuated so that the blood velocities, within the internal and external eye artery portions 46, 48, are sequentially measured. The depths of external and internal optic nerve canal's entrances are determined by increasing $R_E$ from the values between those selected at 106 and the values selected at 112 while observing the blood velocity pulsation of FIG. 5. The blood velocity pulses have smaller amplitudes inside the optic nerve canal.

Then at step 120 the depths $R_1$ and $R_2$ of respectively the external and internal optic nerve canal entrances are determined. This is done by observing a decrease in the amplitudes of the blood velocity pulses, as shown in FIG. 5, and typical for measurements made inside the optic nerve canal in comparison with the amplitudes of blood velocity pulses from outside the optic nerve canal.

After that, at step 122 the final value of $R_E$ and $R_I$ are set using the criteria $R_E<R_1$ and $R_I>R_2$. Once the position of the ultrasonic transducer is determined and set a measurement of the internal and external blood velocities can be made as described above. A determination of the intracranial pressure $Po_i$ is obtained when the pulsatility index measurements are the same.

As shown in FIG. 3, periodical autocalibration and continuous ICP monitoring procedures 125 are also added to the algorithm of non-invasive absolute ICP continuous monitoring apparatus.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method for continuously obtaining an indication of intracranial pressure, comprising the steps of:
   A. measuring the pulsatility index of blood flow in the intracranial portion of an eye artery (P.I.(int)) by use of an ultrasonic Doppler device;
   B. measuring the pulsatility index of blood flow in the extracranial portion of an eye artery (P.I.(ext)) by use of the ultrasonic Doppler device;
   C. applying an external pressure against an eye and measure said external pressure applied against the eye by use of an inflation device;
   D. calculating a ratio of P.I.(ext) to P.I.(int) by a processor;
   E. calculating a conversion factor to convert the ratio of P.I.(ext) to P.I.(int) into an absolute intracranial pressure by said processor, wherein said conversion factor is equal to the external pressure measured which causes said ratio of P.I.(ext) to P.I.(int) to become equal one (1); and
   F. repeating steps A, B, and D and determine intracranial pressure (ICP) by applying said conversion factor to the calculated ratio of P.I.(ext) to P.I.(int) by said processor.

2. The method of claim 1 wherein steps A to F are periodically repeated.

3. The method of claim 2 further comprising the step of:
   J. determining whether the conversion factor is stable by comparing the value of the conversion factor calculated in step E in repeated measurements and calculations, wherein the conversion factor is deemed stable when there is an insubstantial change in the value of the conversion factor calculated in step E.

4. The method of claim 3 further comprising the step of:
   K. determining that the conversion factor is stable if there is an insubstantial change in the value of the conversion factor calculated in step E.

5. The method of claim 1, wherein the ultrasonic Doppler device is coupled with a depth control network,
   and wherein the depth control network enabling the non-invasive invasive ultrasonic Doppler device to sequentially measure the pulsatility index of blood flow in the intracranial portion and extracranial portion of said eye artery.

6. A method for continuously obtaining an indication of intracranial pressure, comprising the steps of:
   A. measuring the pulsatility index of blood flow in the intracranial portion of an eye artery (P.I.(int));
   B. measuring the pulsatility index of blood flow in the extracranial portion of an eye artery (P.I.(ext));
   C. applying an external pressure against an eye and measure said external pressure applied against the eye;
   D. calculating a ratio of P.I.(ext) to P.I.(int);
   E. if the ratio of P.I.(ext) to P.I.(int) does not equal to one (1), increasing the external pressure, and repeating steps C, D, and E until the ratio of the ratio of P.I.(ext) to P.I.(int) equals to one (1); if the ratio of P.I.(ext) to P.I.(int) equals to one (1), calculating a conversion factor to convert the ratio of P.I.(ext) to P.I.(int) into an absolute intracranial pressure, wherein said conversion factor is equal to the external pressure measured, and going to step F; and
   F. repeating steps A, B, and D and determine intracranial pressure (ICP) by applying said conversion factor to the calculated ratio of P.I.(ext) to P.I.(int).

7. The method of claim 6, wherein the external pressure in step E is increased from 0 mmHg to 25.0 mmHg.

8. The method of claim 7, wherein the external pressure in step E is increased step-by-step at 5.0 mmHg increments.

* * * * *